United States Patent [19]

Hughes et al.

[11] Patent Number: 5,401,807
[45] Date of Patent: Mar. 28, 1995

[54] PROCESS OF INCREASING THE MOLECULAR WEIGHT OF WATER SOLUBLE ACRYLATE POLYMERS BY CHAIN COMBINATION

[75] Inventors: Kathleen A. Hughes; Graham Swift, both of Blue Bell, Pa.

[73] Assignee: Rohm and Haas Company, Philadelphia, Pa.

[21] Appl. No.: 958,064

[22] Filed: Oct. 8, 1992

[51] Int. Cl.⁶ .................. C08G 81/02; C08G 81/00
[52] U.S. Cl. .................. 525/327.5; 525/263; 525/327.4; 525/329.7; 525/329.8; 525/330.3; 525/330.4; 525/387
[58] Field of Search .............. 525/387, 263, 327.4, 525/329.7, 327.5, 330.3, 330.4

[56] References Cited

U.S. PATENT DOCUMENTS

| | | | |
|---|---|---|---|
| 3,880,791 | 4/1975 | Marcozzi | 525/293 |
| 4,412,028 | 10/1983 | Lundberg | 524/364 |
| 4,659,793 | 4/1987 | Yang | 526/91 |
| 4,837,272 | 6/1989 | Kelley | 525/59 |
| 4,873,289 | 10/1989 | Lindner | 525/293 |
| 4,910,250 | 3/1990 | Saotome | 524/556 |
| 5,096,947 | 3/1992 | Bowen | 524/58 |
| 5,194,516 | 3/1993 | Fisher | 525/387 |

FOREIGN PATENT DOCUMENTS

| | | |
|---|---|---|
| 97495 | 6/1983 | European Pat. Off. . |
| 124913 | 1/1984 | European Pat. Off. . |
| 208945 | 6/1986 | European Pat. Off. . |

*Primary Examiner*—Fred Zitomer
*Attorney, Agent, or Firm*—James G. Vouros

[57] ABSTRACT

A method has been discovered for generating free radicals at saturated carbon atoms on the backbone of acrylate polymers or copolymers. This method is useful for combining at least two polymer chains at the free radical sites on each polymer chain to form a polymer or copolymer product with increased molecular weight and a controlled degree of branching. The polymers and copolymers produced by this process are useful as antiscalants, dispersants, incrustation inhibitors and superabsorbants. They are particularly useful in detergent and cleaning applications.

15 Claims, No Drawings

PROCESS OF INCREASING THE MOLECULAR WEIGHT OF WATER SOLUBLE ACRYLATE POLYMERS BY CHAIN COMBINATION

A method has been discovered for generating free radicals at saturated carbon-carbon bonds on the backbone of acrylate polymers. This method is useful for combining at least two polymer chains at the free radical sites to form a polymer or copolymer product with increased molecular weight. The polymers and copolymers produced by this process are useful as antiscalants, dispersants, incrustation inhibitors and superabsorbants. They are particularly useful in detergent and cleaning applications.

BACKGROUND OF THE INVENTION

Acrylate polymers and copolymers have many uses, for example as antiscalants, dispersants, incrustation inhibitors, superabsorbants and in detergent and cleaning applications in most of these uses the performance of the acrylate polymer is directly related to its molecular weight and structure. Low molecular weight acrylate polymers may perform differently than high molecular weight acrylate polymers while linear acrylate polymers may perform differently than branched acrylate polymers.

Previously, the molecular weight of acrylate polymers has been controlled by varying the polymerization conditions of the acrylate polymers to achieve the desired molecular weight. Similarly, the structure of acrylate polymers can be controlled by varying the polymerization conditions, however this is difficult and generally leads to either a linear polymer, a highly branched polymer or a gelled (very highly branched) polymer.

The present invention now provides a way to increase the molecular weight of acrylate polymers, after they have been polymerized, using a chain combination reaction. The present invention provides a way to combine polymer chains of known molecular weights to form a polymer product of higher molecular weight. The present invention allows for the formation of a final polymer product with a well defined molecular weight and composition. In addition, the present invention allows for the formation of final acrylate polymers with "controlled" degrees of branching. For example, linear polymer chains can be attached to other linear polymer chains in a controlled fashion to form acrylate polymers with different degrees of branching, ranging from slightly branched to highly branched.

SUMMARY OF THE INVENTION

This invention relates to an aqueous method where the amount of free radicals generated on an acrylate polymer chain can be controlled by varying pH, initiator concentration, reaction time and molecular weight of the acrylate polymer. Once free radicals have been generated on acrylate polymer chains in a controlled fashion, at least two polymer chains can then be combined by reacting at the free radical sites on each chain. The at least two polymer chains can be compositionally the same, compositionally different, or a combination thereof.

DETAILED DESCRIPTION OF THE INVENTION

It has been discovered that the molecular weight of acrylate polymers can be increased and the degree of branching can be controlled by generating free radicals at saturated carbon atoms along acrylate polymer chains and then combining at least two of the polymer chains at the free radical sites on each chain. The result of this chain combination reaction is the formation of a polymer product with a higher molecular weight than the starting acrylate polymer and the formation of an acrylate polymer with a controlled degree of branching.

In the method of the present invention, an aqueous solution of a starting acrylate polymer, copolymer, or a combination thereof, is contained in a reaction vessel. The pH of the aqueous solution is adjusted and maintained at the adjusted pH throughout the reaction. The aqueous reaction solution is heated and an initiator solution is fed into the reaction vessel.

The starting acrylate polymer can be prepared according to techniques well known to those skilled in the art, for example, those described in U.S. Pat. No. 4,314,044 and U.S. patent application Ser. No. 502,100, now U.S. Pat. No. 5,244,988 commonly assigned to the same assignee as the present invention and herein incorporated by reference. The starting acrylate polymer can also be any commercially available water soluble acrylate polymer or copolymer, for example, those sold under the trade name Acusol ® by Rohm and Haas Company, Sokalan ® by BASF or Goodrite ® K resins by Goodrich.

Acrylate polymers particularly useful as starting acrylate polymers include polymers and copolymers polymerized from monomers of ethylenically unsaturated monocarboxylic acids containing from 3 to 8 carbon atoms per molecule and ethylenically unsaturated dicarboxylic acids containing from 4 to 8 carbon atoms per molecule. These monocarboxylic acids and dicarboxylic acids include their alkali metal and ammonium salts, and the anhydrides of the cis dicarboxylic acids. Examples of the monocarboxylic acids include acrylic acid, methacrylic acid, vinylacetic acid, crotonic acid and acryloxypropionic acid. Acrylic acid is preferred. Examples of suitable dicarboxylic monomers include maleic acid, itaconic acid, mesaconic acid, fumaric acid, citraconic acid, tetrahydrophthalic acid, tetrahydrophthalic anhydride and maleic anhydride. Maleic anhydride is preferred among the dicarboxylic monomers.

In addition, the starting acrylate polymer may be composed of up to 70 percent by weight of carboxyl-free monoethylenically unsaturated monomers which include alkyl esters of acrylic or methacrylic acids such as methyl acrylate, ethyl acrylate, butyl acrylate, methyl methacrylate, ethyl methacrylate, butyl methacrylate and isobutyl methacrylate; hydroxyalkyl esters of acrylic or methacrylic acids such as hydroxyethyl acrylate, hydroxypropyl acrylate, hydroxyethyl methacrylate, and hydroxypropyl methacrylate; acrylamide, methacrylamide, N-tertiary butyl acrylamide, N-methyl acrylamide, N,N-dimethyl acrylamide; acrylonitrile, methacrylonitrile, allyl alcohol, allyl sulfonic acid, allyl phosphonic acid, vinylphosphonic acid, dimethylaminoethyl acrylate, dimethylaminoethyl methacrylate, phosphoethyl methacrylate, N-vinyl pyrollidone, N-vinylformamide, N-vinylimidazole, ethylene glycol diacrylate, trimethylolpropane triacrylate, diallyl phthalate, vinyl acetate, styrene, vinylsulfonic acid and its salts, and 2-acrylamido-2-methylpropanesulfonic acid and its salts. The amount of these other monomers included in the composition of the starting acrylate polymer can be up to 70 percent by weight as long as the starting acrylate polymer or copolymer remains water soluble.

It is preferable the starting acrylate polymer is polyacrylic acid or a copolymer of acrylic acid and maleic acid or anhydride. In addition, it is preferable that the molecular weight of the starting acrylate polymer or copolymer be from about 500 to about 100,000, more preferably from about 1,000 to about 50,000, and even more preferably from about 2,000 to about 25,000.

One advantage of the present invention is that the chain combination reaction can be carried out in the same reaction vessel the starting acrylate polymer was polymerized, without any additional separation or purification steps. It is preferred that the starting acrylate polymer be linear and have a low degree of branching.

The concentration of the starting acrylate polymer in the aqueous reaction solution can be from about 10 to about 80, preferably 30 to about 60 weight percent based on the total weight of the reaction solution. The pH of the reaction solution can be adjusted with, for example, ammonium hydroxide or an alkali metal base such as NaOH, KOH and LiOH, preferably sodium hydroxide. The base is preferably added as an aqueous solution. Once the pH has been initially adjusted, the base can be either added at certain intervals or continuously fed into the aqueous reaction solution to maintain the pH at the desired level throughout the reaction.

The aqueous reaction solution can initially contain only one type of starting acrylate polymer and therefore the process of the present invention leads to an acrylate polymer product compositionally the same as the starting acrylate polymer but with a higher molecular weight. The initial aqueous solution can also contain starting acrylate polymers of different compositions. Besides being in the initial aqueous solution, portions of the starting acrylate polymers or copolymers may be added or fed continuously into the reaction vessel during the chain combination reaction.

The chain combination reaction is also useful for combining nonacrylate polymers or copolymers with starting acrylate polymers or copolymers. The nonacrylate polymers or copolymers can be initially contained in the reaction vessel, fed into the reaction vessel during the chain combination reaction, or a combination thereof. When additional non-acrylate polymer or copolymers are added to the reaction vessel, they are preferably polymerized from the non-carboxylic monomers listed above.

As a further alternative, monomer may be added to the reaction vessel. Monomer may be contained in the initial aqueous solution, added during the chain combination reaction or a combination thereof. When monomer is added, it polymerizes via a free radical polymerization and the free radical site on the polymerizing monomer chain can then react with free radical sites generated on the starting acrylate polymer. This leads to the combination of the chain formed from the monomer and the starting acrylate polymer chain. When monomer is added to the reaction vessel, the same monomers listed above for the starting acrylate polymer or copolymer are preferable.

The pH has been found to have a dramatic effect on the chain combination reaction. The chain combination reaction can be run at a pH of from about 1 to 11, preferably 3 to 7, and depending on the pH, the molecular weight of the final product can be varied. It has been found that the maximum increase in molecular weight can be achieved at a pH of about 5.

The chain combination reaction is carried out in the presence of a water soluble initiator. Such polymerization initiators are well known to one skilled in the art and include hydrogen peroxide, t-butyl hydroperoxide, sodium persulfate, potassium persulfate, ammonium persulfate, sodium perphosphate, ammonium perphosphate, potassium perphosphate, or combinations thereof. The initiator concentration can be from about 0.5 to about 40%, preferably from about 1 to about 20% and even more preferably from about 1 to about 10% based on the total weight of the starting acrylate polymer.

If monomer is added to the reaction vessel, in addition to the initiators listed above, other initiators can be added to the reaction vessel for the polymerization of the monomer. An example of an initiator for the polymerization of the monomer is 2,2-azobis(cyanovaleric acid). Initiators for the polymerization of the monomer can be the only initiator used whereby free radicals on the starting acrylate polymer chain are generated by the reaction of the starting acrylate polymer chain with the chain polymerizing from the monomers. As an alternative, initiators for the polymerization of the monomer can be used in combination with initiator for the starting acrylate polymer.

Besides the pH, the molecular weight of the final chain combination product is also dependent on the concentration of the initiator and the reaction time. It has been found that at a given pH, the chain combination reaction time is dependent on the half life of the initiator used. The time and temperature of the chain combination reaction should be from about 1 to about 10 hours, preferably from about 2 to about 5 hours per half life of the initiator to achieve the maximum molecular weight value.

The above polymer products of the chain combination reaction are useful as detergent and cleaning agent additives, superabsorbants, thickeners and gelling agents in, for example cosmetics or paints, dispersants, antiscalants and incrustation inhibitors. They are particularly useful in detergent and cleaning applications.

Detergent compositions containing polymer products of the chain combination reaction may be in any of the usual physical forms, such as powders, beads, flakes, bars, tablets, noodles, liquids, pastes, slurries and the like. The detergent compositions are prepared and utilized in the conventional manner and are usually based on surfactants and, optionally, on either precipitant or sequestrant builders.

Suitable surfactants are, for example, anionic surfactants, such as from $C_8$ to $C_{12}$ alkylbenzenesulfonates, from $C_{12}$ to $C_{16}$ alkanesulfonates, from $C_{12}$ to $C_{16}$ alkylsulfates, from $C_{12}$ to $C_{16}$ alkylsulfosuccinates and from $C_{12}$ to $C_{16}$ sulfated ethoxylated alkanols and nonionic surfactants such as from $C_6$ to $C_{12}$ alkylphenol ethoxylates, from $C_{12}$ to $C_{20}$ alkanol alkoxylates, and block copolymers of ethylene oxide and propylene oxide. Optionally, the end groups of polyalkylene oxides can be blocked, whereby the free OH groups of the polyalkylene oxides can be etherified, esterified, acetalized and/or aminated. Another modification consists of reacting the free OH groups of the polyalkylene oxides with isocyanates. The nonionic surfactants also include $C_4$ to $C_{18}$ alkyl glucosides as well as the alkoxylated products obtainable therefrom by alkoxylation, particularly those obtainable by reaction of alkyl glucosides with ethylene oxide. The surfactants usable in detergents can also have an amphoteric character and they can be soaps.

In general, the surfactants constitute from 2 to 50, preferably 5 to 45 percent by weight of the detergent or cleaning formulation. Liquid detergents usually contain as components liquid or even solid surfactants which are soluble or at least dispersible in the detergent formulation. Surfactants suitable for this purpose are liquid polyalkylene oxides or polyalkoxylated compounds, products that can also be used in powdered detergents.

Examples of sequestrant builders contained in the detergent and cleaning agents of the present invention can include phosphates, specifically, orthophosphates, pyrophosphates and especially sodium tripolyphosphate. Further examples are the zeolites, sodium carbonate, polycarboxylic acids, nitrilotriacetic acid, citric acid, tartaric acid, the salts of the aforesaid acids and the monomeric, oligomeric or polymeric phosphonates.

The amounts of the individual substances used in the preparation of detergent formulations by weight based on the total weight of the detergent formulation are, for example, up to 85 weight percent sodium carbonate, up to 45 weight percent phosphates, up to 40 weight percent zeolites, up to 30 weight percent nitrilotriacetic acid and phosphonates and up to 30 weight percent polycarboxylic acids. Because of the environmental impact caused by the use of phosphates, the phosphate content of detergent and cleaning agent formulations is being reduced so that detergents currently contain less than about 30 weight percent of phosphates or preferably are phosphate-free. In certain liquid detergent markets the use of builders is usually limited to citric acid and its salts or a combination of citrate and fatty acid soap, while in other markets liquid detergent compositions incorporate an intermediate level of soap, about 15 weight percent, or tripolyphosphate, about 20 weight percent, to assist overall cleaning efficacy.

Other common additives to detergent and cleaning agent formulations are bleaching agents, used in an amount of up to 30 weight percent, corrosion inhibitors, such as silicates, used in an amount of up to 25 weight percent and graying inhibitors used in an amount of up to 5 weight percent. Suitable bleaching agents are, for example, perborates, percarbonates or chlorine-generating substances, such as chloroisocyanurates. Suitable silicates used as corrosion inhibitors are, for example, sodium silicate, sodium disilicate and sodium metasilicate Examples of graying inhibitors are carboxymethylcellulose, methylcellulose, hydroxypropylmethylcellulose and graft copolymers of vinyl acetate and polyalkylene oxides having a molecular weight of 1,000 to 15,000. Other common detergent additives optionally used are optical brighteners, enzymes and perfumes. Powdered detergent formulations can also contain up to 50 weight percent of an inert diluent, such as sodium sulfate, sodium chloride, or sodium borate. The detergent formulations can be anhydrous or they can contain small amounts, for example up to 10 weight percent, of water. Liquid detergents can contain up to 80 weight percent water as an inert diluent.

The above-described polymer products of the chain combination reaction can be added to all detergent and cleaning agent formulations and are used in amounts between about 0.5 and 30 weight percent, preferably between about 1 and 15 weight percent, based on the total weight of the formulation. In most cases, particularly when used as soil redeposition inhibitors, the amount of polymer actually used is preferably between about 2 and 10 weight percent, based on the detergent and cleaning agent mixture. Of particular importance is the use of the additives according to the invention in phosphate-free and low-phosphate detergents and cleaning agents, particularly those containing a precipitant builder such as sodium carbonate. The low-phosphate formulations contain up to a maximum of 25 weight percent of sodium tripolyphosphate or pyrophosphate. The polymers prepared according to the invention are preferably used at high concentration in phosphate-free formulations and serve as builders in place of the phosphates.

If desired, the polymers prepared according to the invention can be used in detergent formulations together with other copolymers of acrylic acid and maleic acid, with acrylic acid homopolymers or a combination thereof. The last-mentioned polymers are currently being used as soil redeposition inhibitors in detergent formulations. In addition to the aforementioned polymers, the copolymers of from $C_3$ to $C_8$ monocarboxylic and dicarboxylic acid or maleic anhydride and from $C_1$ to $C_4$ alkyl vinyl ethers are also suitable as soil redeposition inhibitors. The molecular weight of the homopolymers and copolymers is 1,000 to 100,000. If desired, these soil redeposition inhibitors can be used in detergents, together with the polymers or copolymers of this invention, in an amount of up to 20 weight percent based on the total formulation. The polymers of the present invention can be added to detergent formulations in the free acid form or in completely or partly neutralized form.

Other applications for the polymers of this invention include water treatment. Water treatment applications for these polymers include dispersing applications, such as in aqueous clay dispersions for paper making, and anti-nucleating agents where minor amounts of the copolymers can serve as threshold inhibitors for crystal formation or scaling in cooling towers or boilers. When used to inhibit crystal formation or scaling, the water-soluble polymers are often combined with corrosion inhibitors such as inorganic or organic phosphates or phosphonates or metallic salts such as zinc compounds and the like. The polymers of the present invention can be added directly to the aqueous system or they can be added as a concentrated aqueous composition wherein the copolymer is present in the composition at a level of from 20% to 60% by weight.

The invention is further illustrated by the following examples which are intended to be purely exemplary. All percentages are by weight unless otherwise specified.

EXAMPLE 1

A. Preparation of Acrylate Polymer-Polyacrylic Acid (General Procedure)

Polyacrylic acids of approximately 10,000 and 20,000 Mw were prepared via a gradual addition aqueous solution polymerization process employing 3-mercaptopropionic acid (MPA) as the chain transfer agent. Acrylic acid (AA), an aqueous solution of sodium persulfate (NaPS), and the MPA were added linearly and separately to a flask containing a water heel charge at 90° C. AA, NaPS, and MPA feed times were 2, 2, and 1.75 hours, respectively. After completion of the feeds, the batch was held at 90° C. for 30 minutes. In cases where the residual AA was higher than desired, 4,4'-azobis(4-cyanovaleric acid) in water was added over 30 minutes at 90° C., after which the mixture was held at 90° C. for one hour.

B. Chain Combination Reaction

The chain combination reaction was carried out by first charging the reaction vessel with the starting polymer solution and adding sodium hydroxide (50%) to bring the solution to the desired pH. pH was monitored with a pH electrode connected to a Chemcadet ® (Cole Parmer) pH meter/controller. If necessary, water was added to adjust the solids level. The solution was then heated to 90° C. An aqueous solution of NaPS was then fed into the solution linearly over 30 minutes, during which time the pH was monitored and maintained at the desired point by the addition of NaOH solution (via a pump connected to the Chemcadet or manually via an addition funnel). The reaction solution was then held at 90° C. for one hour.

Example 2

To a one liter, four-neck, round bottom flask equipped with a mechanical stirrer, heating mantle, temperature controller, and reflux condenser was added 200.00 grams of polyacrylic acid solution neutralized to pH 4.8 (34% solids; Mw=21,300, Mn=9430, Mw/Mn=2.26). The solution was heated to 90° C. and then a solution of 2.64 grams of sodium persulfate dissolved in 7.36 grams of water was fed into the reaction vessel over 15 minutes via a syringe pump. Once the addition was complete, the reaction solution temperature was maintained for an additional 45 minutes at 90° C., then it was allowed to cool.

The final pH was 4.6; the final measured solids were 34.6%. Molecular weight data of the product was obtained via aqueous gel permeation chromatography (GPC). The weight average molecular weight (Mw) was 120,000, the number average molecular weight (Mn) was 10,600 and Mw/Mn was 11.31.

Example 3

To a one liter flask equipped as in Example 2, was added 200.00 grams of poly(acrylic acid) solution neutralized to pH 4.8 (34% solids; Mw=21,300, Mn=9430, Mw/Mn=2.26) and 54.4 grams water. The solution was heated to 90° C. and then a solution of 1.06 grams of sodium persulfate dissolved in 8.94 grams of water was fed into the polymer solution over 15 minutes via a syringe pump. The solution temperature was maintained for an additional 45 minutes at 90° C. and then it was allowed to cool.

The final pH was 4.6 and the final solids level was 26.6%. The Mw was 28,200, Mn was 8260 and Mw/Mn was 3.41.

Example 4

To a one liter flask equipped as in Example 2, was added 200.00 grams of a polyacrylic acid solution neutralized to pH 4.8 (34% solids; Mw=21,300, Mn=9430, Mw/Mn=2.26). The solution was heated to 90° C. and then a solution of 1.06 grams of sodium persulfate dissolved in 8.94 grams of water was fed into the reaction vessel over 15 minutes via a syringe pump. The solution was held for an additional 45 minutes at 90° C. and then it was allowed to cool.

The final pH was 4.6, final measured solids were 33.8%, the Mw was 31,200, the Mn was 8480 and Mw/Mn was 3.67.

Example 5

To a one liter flask equipped as in Example 2, was added 1200.00 grams of polyacrylic acid solution neutralized to pH 4.6 (34% solids; Mw=10,900, Mn=7210, Mw/Mn=1.51). The solution was then heated to 90° C. and then a solution of 5.28 grams of sodium persulfate dissolved in 14.72 grams of water was fed into the reaction vessel over 15 minutes via a syringe pump. The solution temperature was maintained for an additional 45 minutes at 90° C. and then it was allowed to cool.

The final pH was 4.4, the final measured solids were 33.4%, the Mw was 125,000, the Mn was 10,800, Mw/Mn=11.53.

Examples 6–15

The pH dependence of persulfate-initiated chain combination reactions starting with either 10,000 or 20,000 Mw polyacrylic acid and 5% sodium persulfate (based on acrylic acid content) was examined in Experiments 6–15. The polyacrylic acid concentrations in the reaction solution varied from 25% to 29% for the 10,000 Mw polyacrylic acid and from 23% to 25% for the 20,000 Mw polyacrylic acid. Table I and Table II contain the results of these Examples.

TABLE I

Effect of pH on Molecular Weight in NaPS-Initiated Chain Combination Reaction of pAA (5 Wt % NaPS on AA)

| Expt. # | Rxn. pH | AA Wt % in Soln. | Mw | Mn | Mw/Mn | |
|---|---|---|---|---|---|---|
|  |  |  | 10,200 | 6740 | 1.58 | starting pAA |
| 6 | 1.0–1.1 | 27.2 | 12,200 | 7330 | 1.66 |  |
| 7 | 3.0–3.2 | 28.7 | 12,900 | 7520 | 1.72 |  |
| 8 | 4.9–5.0 | 27.8 | 16,300 | 7670 | 2.13 |  |
| 9 | 6.9–7.0 | 27.0 | 11,600 | 6900 | 1.68 |  |
| 10 | 8.4–9.8 | 25.3 | 10,200 | 6580 | 1.55 |  |

TABLE II

Effect of pH on Molecular Weight in NaPS-Initiated Chain Combination Reaction of pAA (5 Wt % NaPS on AA)

| Expt. # | Rxn. pH | AA Wt % in Soln. | Mw | Mn | Mw/Mn | |
|---|---|---|---|---|---|---|
|  |  |  | 19,500 | 11,100 | 1.75 | starting pAA |
| 6 | 1.7–2.1 | 25.0 | 32,700 | 14,800 | 2.21 |  |
| 7 | 3.0 | 23.5 | 48,900 | 16,200 | 3.02 |  |
| 8 | 5.0 | 24.8 | 110,000 | 15,800 | 6.96 |  |
| 9 | 7.0 | 24.9 | 31,100 | 13,300 | 2.35 |  |
| 10 | 8.7–10.1 | 23.1 | 22,600 | 12,000 | 1.88 |  |

With both the 10,000 and 20,000 molecular weight polyacrylic acid, the weight average molecular weight peaked at approximately pH 5 while the number average molecular weight remained essentially unchanged over the pH range. At pH 5, the molecular weight of the 10,000 Mw acrylate polymer increased 1.7 fold in Mw during the chain combination reaction. The molecular weight of the 20,000 Mw acrylate polymer increased 5.6 fold in Mw during the chain combination reaction.

The effect of persulfate concentration was also examined using the 20,000 Mw polyacrylic acid starting material. The experiments were done at pH 5 where the maximum increase in molecular weight occurred. Data for these experiments are provided in Table III. Clearly, persulfate concentration had a dramatic effect on branching; at 10% NaPS and 25% pAA, the polymer gelled. Despite the fact that the polymer gelled, it still has utility in the area of superabsorbants.

TABLE III

Effect of NaPS Concentration on Molecular Weight in Chain Combination Reaction of pAA at pH 5

| Expt. # | Wt % NaPS | Rxn. pH | pAA Wt % in Soln. | Mw | Mn | Mw/Mn |
|---|---|---|---|---|---|---|
| Initial | | | | 19,500 | 11,100 | 1.75 |
| 1 | 2 | 5.0 | 24.7 | 29,100 | 13,700 | 2.12 |
| 2 | 5 | 5.0 | 24.8 | 110,000 | 15,80 | 6.96 |
| 3 | 10 | 5.0–5.1 | 25.2 | — | gelled | — |

The effect of hold time on molecular weight during the post-polymerization reaction at pH 5 was examined using the 20,000 Mw polyacrylic acid staring material and 5% NaPS; polyacrylic acid concentration was 24.5%. Mw leveled out after approximately two hours. The leveling out of Mw correlated well with the point at which the persulfate concentration in solution is approaching zero.

The following Tables exemplify the utility of the polymers products of the chain combination reaction.

TABLE IV

Calcium Sequestration and Tolerance

| Sample | Mw | Mw/Mn | Calcium Sequestration[1] (mg CaCO$_3$/g) | Calcium Tolerance[2] (mg CaCO$_3$/g) |
|---|---|---|---|---|
| A-Initial PAA | 10,900 | 1.51 | 407.1 | 387 |
| 1A[3] | 16,700 | 2.18 | 397.9 | 430 |
| 2A | 20,600 | 2.25 | 393.5 | 365 |
| 3A | 125,000 | 11.53 | 381.5 | 450 |
| 4A | 142,000 | 12.97 | 379.6 | 430 |
| B-Initial PAA | 21,300 | 2.26 | 431.5 | 440 |
| 1B[3] | 28,200 | 3.41 | 415.2 | 450 |
| 2B | 31,200 | 3.67 | 414.4 | 410 |
| 3B | 120,000 | 11.31 | 412.3 | <240 |
| 4B | 123,000 | 11.04 | 407.3 | 450 |
| Polyacrylic acid | 4,500 | | 350.0 | 600 |
| AA/MAL[4] | 30,000 | | 423.5 | 260 |

[1]Determined with a Ca ion selective electrode at pH = 10, RT.
[2]Determined by turbidity measurement (5 ntu end-point) in tap water, ambient pH and temperature.
[3]Sample numbers 1–4 represent the product of the chain combination reaction of the initial PAA (A or B).
[4]Acrylic acid/maleic anhydride copolymer

TABLE V

Clay Soil Detergency Results U.S. Test Conditions

| Polymer in No-P Detergent | | Std. Dev. | Delta (PAA 4,500) |
|---|---|---|---|
| FABRIC = Cotton (soiled) | | | |
| | Detergency | | |
| Polyacrylic acid (4,500) | 27.9 | 1.7 | — |
| 1B | 27.8 | 2.1 | −0.1 |
| 2B | 28.1 | 0.9 | 0.2 |
| FABRIC = White Cotton (Redep) | | | |
| | Whiteness Index | | |
| Polyacrylic acid (4,500) | 63.3 | 1.2 | — |
| 1B | 63.9 | 1.4 | 0.6 |
| 2B | 63.0 | 0.7 | −0.3 |

[1]Clay Soil Removal/Redeposition Test-(Skippack clay/presoiled) - HBB Terg: 40° C., 100 ppm (tap water), 5 cloths (3 soiled/pot) .13% det, 3% pol., 12 min wash/ 3 min. rinse, 100 rpm.

TABLE VI

Magnesium Silicate Inhibition Test Results[1]

| | Total Hardness (ppm) | | | | | | | | |
|---|---|---|---|---|---|---|---|---|---|
| | 25 | 35 | 45 | 60 | 85 | 110 | 130 | 160 | 200 |
| Sample | % Transmittance[2] | | | | | | | | |
| PAA (4,500) | 99 | 99 | 99 | 99 | 98 | 98 | 98 | 98 | 98 |
| PAA (10,000) | 100 | 100 | 100 | 100 | 100 | 100 | 100 | 100 | 100 |
| AA/MAL | 100 | 100 | 100 | 99 | 97 | 96 | 95 | 95 | 94 |
| 1B | 100 | 100 | 99 | 98 | 98 | 98 | 98 | 98 | 97 |
| 2B | 100 | 100 | 99 | 99 | 99 | 98 | 98 | 98 | 97 |
| 3A | 98 | 98 | 98 | 97 | 97 | 97 | 97 | 97 | 97 |
| no polymer | 98 | 97 | 94 | 93 | 90 | 87 | 85 | 83 | 77 |

[1]Test conditions: 85° C., hardness - 1:3 (Ca/Mg), 10,000 ppm detergent (11.2% surfactant/10% Na$_2$CO$_3$/15% Na silicate 2% polymer/ 61.8% H$_2$O).
[2]Higher transmittance desirable since it indicates less formation of magnesium silicate precipitate.

TABLE VII

Incrustation Test Results - European Wash Conditions[1]

| Sample | Molecular Weight | % Average Incrustation | Standard Deviation |
|---|---|---|---|
| Incrustation on Krefeld | | | |
| AA/MAL | 30,000 | 4.78 | 0.11 |
| 1B | 28,200 | 4.20 | 0.11 |
| 2B | 31,200 | 4.11 | 0.05 |
| 3A | 125,000 | 3.92 | 0.16 |
| Incrustation on Terry Cloth | | | |
| AA/MAL | 30,000 | 2.92 | 0.32 |
| 1B | 28,200 | 2.44 | 0.08 |
| 2B | 31,200 | 1.98 | 0.05 |
| 3A | 125,000 | 2.17 | 0.10 |

[1]European mini-washers, 0.65% No-P detergent base, 4% polymer, 90° C., 300 ppm hardness, 22 cycles terry cloth/Krefeld fabric/ballast, ashed 8 hrs @ 800° C.

TABLE VII

Detergency Results - European Wash Conditions[1]

| Polymer | Average Detergency | standard deviation | delta (no polymer) |
|---|---|---|---|
| Dust-Sebum on Cotton | | | |
| no polymer | 22.4 | 0.7 | — |
| AA/MAL | 24.0 | 0.7 | 1.6 |
| 1B | 23.1 | 1.9 | 0.7 |
| 2B | 24.8 | 1.2 | 2.4 |
| 3A | 25.3 | 1.0 | 2.9 |
| 3B | 24.2 | 0.4 | 1.8 |
| Dust-Sebum on PE/Cot | | | |
| no polymer | 24.2 | 0.5 | — |
| AA/MAL | 25.2 | 0.4 | 1.0 |
| 1B | 25.6 | 0.8 | 1.4 |
| 2B | 25.6 | 0.5 | 1.1 |
| 3A | 24.6 | 0.7 | 0.4 |
| 3B | 24.2 | 0.9 | 0 |

TABLE VII-continued

| | Detergency Results - European Wash Conditions[1] | | |
|---|---|---|---|
| Polymer | Average Detergency | standard deviation | delta (no polymer) |
| Clay on Cotton | | | |
| no polymer | 24.8 | 1.0 | — |
| AA/MAL | 26.6 | 1.0 | 1.8 |
| 1B | 26.2 | 0.9 | 1.4 |
| 2B | 25.1 | 1.7 | 0.3 |
| 3A | 26.2 | 0.7 | 1.4 |
| 3B | 22.7 | 0.8 | −2.1 |
| Red Wine on Cotton | | | |
| no polymer | 27.1 | 0.7 | — |
| AA/MAL | 26.9 | 0.3 | −0.2 |
| 1B | 27.9 | 0.7 | 0 |
| 2B | 25.8 | 0.3 | −1.3 |
| 3A | 27.4 | 0.5 | 0.3 |
| 3B | 25.9 | 0.5 | −1.2 |

[1]European mini-washers, 0.65% No-P detergent base, 4% polymer 60° C., 300 ppm hardness, 1 cycle 4 cloths each soil + ballast.

Other embodiments of the invention will be apparent to those skilled in the art from a consideration of this specification or practice of the invention disclosed. It is intended that the specification and examples be considered as exemplary only, with the true scope and spirit of the invention indicated by the following claims.

We claim:

1. A method of increasing molecular weight comprising:
   a) forming an aqueous solution containing at least two water soluble polymer chains, wherein at least one of the water soluble polymer chains is a water soluble acrylate polymer;
   b) adjusting and maintaining the aqueous solution pH from about 1 to about 11;
   c) gradually feeding one or more water soluble initiators to the aqueous solution and generating one or more free radicals at saturated carbon atoms on at least two of the water soluble polymer chains, at least one of the water soluble polymer chains being the acrylate polymer; wherein when the aqueous solution pH is in the range of from about 3 to 7, the total concentration of the one or more water soluble initiators is from about 0.5 to 5 weight percent, based on the weight of the water soluble acrylate polymer; and
   d) combining the acrylate polymer chain with one or more of the water soluble polymer chains at the free radical sites to form a water soluble polymer product with a predetermined weight average molecular weight equal to or less than about 142,000, and wherein the molecular weight of the polymer product is greater than the acrylate polymer.

2. The method of claim 1 wherein the acrylate polymer is composed of polymerized monomeric units selected from the group consisting of an ethylenically unsaturated monocarboxylic acid containing from 3 to 8 carbon atoms per molecule, an ethylenically unsaturated dicarboxylic acid containing from 4 to 8 carbon atoms per molecule, the alkali metal and ammonium salts of the monocarboxylic acid and the dicarboxylic acid, the anhydrides of the cis dicarboxylic acids, and a combination thereof.

3. The method of claim 2 wherein the acrylate polymer contains polymerized monomeric units of carboxyl-free monoethylenically unsaturated monomers.

4. The method of claim 2 wherein the ethylenically unsaturated monocarboxylic acid is selected from the group consisting of acrylic acid, methacrylic acid, vinyl acetic acid, crotonic acid, acryloxypropionic acid and a combination thereof.

5. The method of claim 1 wherein the acrylate polymer is polyacrylic acid.

6. The method of claim 2 wherein the ethylenically unsaturated dicarboxylic acid is selected from the group consisting of maleic acid, itaconic acid, mesaconic acid, fumaric acid, citraconic acid, tetrahydrophthalic acid, tetrahydrophthalic anhydride and maleic anhydride.

7. The method of claim 1 wherein the acrylate polymer is a copolymer of acrylic acid and maleic anhydride.

8. The method of claim 3 wherein the carboxyl-free monoethylenically unsaturated monomer is selected from the group consisting of alkyl esters of acrylic and methacrylic acids; hydroxyalkyl esters of acrylic and methacrylic acids; acrylamide, methacrylamide, N-tertiarybutyl acrylamide, N-methyl acrylamide, N,N-dimethyl acrylamide; acrylonitrile, methacrylonitrile, allyl alcohol, allyl sulfonic acid, allyl phosphonic acid, vinylphosphonic acid, dimethylaminoethyl acrylate, dimethylaminoethyl methacrylate, phosphoethyl methacrylate, N-vinyl pyrollidone, N-vinylformamide, N-vinylimidazole, ethylene glycoldiacrylate, trimethylolpropane triacrylate, diallyl phthalate, vinyl acetate, styrene, vinylsulfonic acid and its salts, and 2-acrylamido-2-methylpropanesulfonic acid and its salts.

9. The method of claim 1 wherein the acrylate polymer is present in the aqueous solution at a concentration of from about 10 to 80 percent based on the total weight of the reaction solution.

10. The method of claim 1 wherein the acrylate polymer is present in the aqueous solution at a concentration of from about 30 to 60 percent based on the total weight of the reaction solution.

11. The method of claim 1 wherein the aqueous solution pH is adjusted by adding an alkali metal base, ammonium hydroxide, or a combination thereof.

12. The method of claim 11 wherein the aqueous solution pH is adjusted to about 3 to about 7.

13. The method of claim 1 wherein the aqueous solution is heated from about 80° to about 125° C.

14. The method of claim 13 wherein the initiator is sodium persulfate.

15. The method of claim 1 wherein the polymer product has a weight average molecular weight equal to or less than about 48,900.

* * * * *